United States Patent [19]
Nazareth et al.

[11] Patent Number: 6,046,057
[45] Date of Patent: *Apr. 4, 2000

[54] ANALYTE ASSAYING DEVICE

[75] Inventors: Albert R. Nazareth, Mercerville; Mary Beth Boyle, Pennington, both of N.J.; Yea-Shun Cheng, Doylestown, Pa.

[73] Assignee: Carter-Wallace, Inc., New York, N.Y.

[*] Notice: This patent is subject to a terminal disclaimer.

[21] Appl. No.: 08/957,746

[22] Filed: Oct. 24, 1997

[51] Int. Cl.⁷ .................................................. G01N 33/558
[52] U.S. Cl. .............................. 436/514; 422/55; 422/56; 422/57; 422/58; 435/287.1; 435/287.2; 435/287.7; 435/287.9; 435/805; 435/810; 435/970; 436/65; 436/164; 436/169; 436/510; 436/518; 436/524; 436/528; 436/805; 436/810; 436/814; 436/818
[58] Field of Search .................................. 422/55, 56, 57, 422/58, 61; 435/287.1, 287.2, 287.7, 287.9, 805, 810, 970; 436/164, 169, 65, 510, 514, 518, 524, 528, 805, 810, 814, 818

[56] References Cited

U.S. PATENT DOCUMENTS

| | | |
|---|---|---|
| D. 341,663 | 11/1993 | Coulter . |
| D. 361,842 | 8/1995 | Nazareth et al. . |
| D. 369,868 | 5/1996 | Nazareth et al. . |
| 3,655,515 | 4/1972 | Noorlander . |
| 4,861,711 | 8/1989 | Friesen et al. . |
| 4,999,285 | 3/1991 | Stiso . |
| 5,039,607 | 8/1991 | Skold et al. . |
| 5,075,078 | 12/1991 | Osikowicz et al. . |
| 5,079,142 | 1/1992 | Coleman et al. . |
| 5,137,806 | 8/1992 | Ullman et al. ............................ 435/7.9 |
| 5,137,808 | 8/1992 | Ullman et al. ............................ 435/7.9 |
| 5,141,850 | 8/1992 | Cole et al. . |
| 5,160,486 | 11/1992 | Schlipfenbacher et al. . |
| 5,164,294 | 11/1992 | Skold et al. . |
| 5,238,847 | 8/1993 | Steinbiss et al. . |
| 5,248,619 | 9/1993 | Skold et al. . |
| 5,354,692 | 10/1994 | Yang et al. . |
| 5,356,782 | 10/1994 | Moorman et al. . |
| 5,384,264 | 1/1995 | Chen et al. . |
| 5,403,706 | 4/1995 | Wilk et al. . |
| 5,559,041 | 9/1996 | Kang et al. ............................ 436/518 |
| 5,602,040 | 2/1997 | May et al. . |
| 5,622,871 | 4/1997 | May et al. . |
| 5,739,041 | 4/1998 | Nazareth et al. ....................... 436/518 |

FOREIGN PATENT DOCUMENTS

| | | |
|---|---|---|
| 0 560 411 A3 | 4/1988 | European Pat. Off. . |
| WO 92/01226 | 1/1992 | WIPO . |
| WO 94/01775 | 1/1994 | WIPO . |
| WO 94/06012 | 3/1994 | WIPO . |
| WO 94/15215 | 7/1994 | WIPO . |

*Primary Examiner*—Christopher L. Chin
*Attorney, Agent, or Firm*—Watov & Kipnes, P.C.

[57] ABSTRACT

The invention is an improved single-step test device for detecting the presence of a pre-selected analyte in a urine stream. The device includes a hollow rectangular outer casing and an assay material disposed within co-joined upper and lower sections of the casing. The outer casing includes a urine inlet port; a viewing window in the upper section; at least the upper section consisting of transparent material; and may also include at least one drainage vent spaced about the urine inlet port. The assay material is a sorptive material including: a urine sample application region adjacent to, and in fluid communication with the urine inlet port; a capture region adjacent to the viewing window; and a fluid flow path for transporting a liquid sample between the urine sample application region and the analyte capture region. The flow of urine in the fluid path is observable through the transparent upper section for confirming a test is operative. The drainage vent is located to permit excess urine entering the casing from the urine stream to exit the casing thereby to minimize hydraulic pressure induced flooding of the assay material disposed within the casing and to reduce the frequency of false test results.

23 Claims, 6 Drawing Sheets

ANALYTE ASSAYING DEVICE

RELATED APPLICATIONS AND PATENTS

The present invention is related to co-pending utility application Ser. No. 08/432,890, entitled "IMPROVED DIAGNOSTIC DETECTION DEVICE, filed May 2, 1995 now U.S. Pat. No. 5,739,041; and to Ser. No. 08/432,894, entitled "Improved Diagnostic Device And Method", filed May 2, 1995; and to Ser. No. 08/434,342, entitled "A Method of Making A Laminated Substrate and an Apparatus For Marking The Substrate With Reagent", filed May 2, 1995; and to Design application Ser. No. 29/068,448, filed Apr. 8,1997 , abandoned and continued as Serial No. 906, 638 filed Aug. 7, 1997 now U.S. Pat. No. 5,846,836 now design U.S. Pat. No. Des. 390,667, for "DIAGNOSTIC DETECTION DEVICE"; all of which are incorporated herein in their entirety to extent they do not conflict herewith.

FIELD OF THE INVENTION

This invention relates to an improved device for assaying a pre-selected analyte, such as an antigen, in a body fluid, such as urine.

BACKGROUND OF THE INVENTION

A variety of ligand-receptor assays have been developed to detect the presence of a preselected analyte in body fluid. Typically, these assays involve antibody-antigen interactions, synthetic conjugates comprising radioactively, enzymatically, spectroscopically, or visually observable tags, and specially designed reactor chambers. In most assays, there is a receptor (e.g., an antibody) that is specific for the pre-selected analyte (e.g., an antigen), and a means for detecting the presence and/or amount of a resulting receptor-analyte (e.g., antibody-antigen) complex. Most current assays are designed to make a quantitative determination, but in many circumstances all that is required is a qualitative result, i.e., a positive or negative signal. Examples of such qualitative assays include, for example, pregnancy tests, ovulation tests as well as a variety of other types of urine analysis. In these tests, visually observable signals such as the presence of agglutination of a color change are preferred.

The assays optimally are performed using single-step devices wherein the only step the user need perform prior to observation of the result is application of the sample to be assayed onto the device. Single-step devices, therefore, obviate the necessity of performing, subsequent to the application of the sample, a series of manipulations which may be time consuming and/or may introduce errors in the end result. Accordingly, several single-step devices, for example those described in International Application Nos. WO 88/08534, published Nov. 3,1988, have been developed and are commercially available.

The single-step device described in International Application Published No. WO 88/08534 comprises a hollow casing containing a porous assay material communicating with the exterior of the casing via a fluid sample receiving member. During operation, the user applies the fluid test sample onto the fluid sample receiving member protruding out of the casing. Thereafter, the fluid sample while traversing the carrier material enters the casing and moves to a capture region disposed upon the carrier material. The capture region comprises a means for binding a pre-selected analyte. When the fluid sample reaches the capture region, assuming that the fluid sample contains the analyte, the analyte binds to the capture region. The bound analyte subsequently can be visualized within the capture region.

It has been found, however, that invalid test results may arise from the use of single-step devices, particularly devices wherein the fluid sample is applied directly from a fluid stream through a urine inlet port defined by the casing onto assay material enclosed therein.

SUMMARY OF THE INVENTION

Accordingly, with the problems in the prior art in mind, it is an object of the present invention to provide an improved single-step detection device for reliably detecting the presence of a pre-selected analyte within a body fluid, when the body fluid, i.e., urine, is applied directly from a fluid stream, i.e., a urine stream, onto assay material disposed within device.

It is another object of the invention to provide a method for detecting a pre-selected analyte using a single-step device of the type described herein.

It is yet another object of the invention to provide a method for producing a single-step detection device of the type described herein.

Yet another object of the invention is to provide a method and apparatus for permitting a user, after applying a fluid sample onto assay material, to immediately know a test is working rather than waiting a substantial time for a test result, if any, to appear in a viewing window of the detection device.

The present invention provides a rapid, sensitive and more reliable device and method for detecting the presence of analytes in a fluid stream. The use of the present device and method provide a system for measuring the presence of a pre-selected analyte in body fluid, specifically urine, which involves a minimal number of procedural steps, and reproducibly yields reliable results even when used by untrained persons.

It has been discovered that during the use of single-step devices, particularly devices wherein the sample of fluid to be assayed is applied directly from a stream of fluid onto assay material enclosed within the device casing, false or otherwise invalid results may arise following hydraulic pressure induced flooding of assay material. The incidence of flooding impairs the reliability, and therefore the commercial value of the test kit. Accordingly, the single-step device and method of the instant invention utilize an improved device casing that minimizes hydraulic pressure induced flooding of the assay material located therein, for thereby substantially increasing the reliability of the test result. More specifically, it has been discovered that introduction of drainage vents in the casing dramatically improves the reliability of the test kit and virtually eliminates the incidence of flooding.

In its broadest aspect, the invention provides a device having an outer casing and an assay material disposed within the casing for detecting the presence of an analyte in a urine stream. The assay material defines a capture region for binding the analyte. The outer casing defines the following features which include a hollow housing enclosing the assay material; a urine inlet port to permit urine applied directly from a urine stream to enter the casing and contact the assay material disposed within the casing; a window spaced apart from the urine inlet port for viewing the capture region; and at least one drainage vent to permit excess urine entering the casing through the urine inlet port to exit the casing thereby to minimize pressure induced flooding of the casing.

In a preferred embodiment, the assay material comprises a sorptive material defining a urine sample application region spaced apart from the capture region. The sorptive material permits the sorptive transport of urine between the urine sample application region and the capture region. Therefore, when urine from a urine stream is directed through the urine inlet port onto the urine sample application region the analyte in the urine moves by sorptive transport from the urine application region to the capture region, whereupon the analyte binds to the capture region.

In another embodiment, the device casing defines three drainage vents spaced about the urine inlet port to permit urine entering the casing via the urine inlet port to exit the casing. The drainage vents, therefore, minimize the build up of urine within the casing and thereby inhibit hydraulic pressure induced flooding of the assay material disposed therein. In another embodiment, the window for viewing the capture region is located on a side of the device casing opposite the urine inlet port.

In another embodiment, the device further comprises a rib member defining a dam positioned within the casing to inhibit hydraulically driven urine from flooding the casing. The rib member may either be defined by an inner surface of the casing formed during the production of the casing or may be a separate component inserted into the device during assembly.

In a preferred aspect, the invention provides a device having an outer casing and an assay material disposed within the casing for detecting the presence of an analyte in a urine stream. The outer casing defining the following features which include: a hollow housing for receiving the assay material; a urine inlet port at a proximal end of the casing to permit urine applied directly from a urine stream to enter the casing; a window at a distal end of the casing for viewing a capture region on the assay material; and at least one drainage vent to permit excess urine entering the casing through the urine inlet port to exit the casing thereby to minimize hydraulic pressure induced flooding of the casing. The assay material enclosed with the casing defines a urine sample application region, an analyte capture region, and a fluid flow path connecting the urine sample application region and the analyte capture region. The urine sample application region is located adjacent to, and in fluid communication with the urine inlet port, whereas the analyte capture region is located adjacent to the viewing window. The fluid flow path transports the urine sample by sorption between the urine sample application region and the capture region such that when a urine stream is directed through the inlet port onto the urine sample application region, the analyte in the urine moves by sorptive transport along the flow path of the assay material to the capture region whereupon the analyte binds to the capture region.

In another aspect, the invention provides a method for detecting the presence of an analyte in a urine stream suspected to contain the analyte. The improvement comprises employing an improved device for the type described herein.

In another aspect, the invention provides a method for producing an improved device for detecting the presence of an analyte in a urine stream. The method comprises the steps of providing an assay material having a capture region for binding the analyte and providing a casing. The casing defines a hollow housing for receiving the assay material, a urine inlet port to permit urine applied directly from a urine stream to enter the casing, a window spaced apart from the urine inlet port for viewing the capture region, and at least one drainage vent to permit urine entering the casing through the urine inlet port to exit the casing thereby to minimize hydraulically induced flooding of the casing. The method further comprises the steps of enclosing the assay material within the casing.

In another preferred embodiment of the invention, the casing defines a hollow housing having an upper section and a lower section joined together and containing the assay material therebetween. The upper section is transparent and includes a window for viewing the capture region. The lower section is preferably opaque, but can also be transparent, and includes a urine inlet port spaced apart from the vertical plane of the window in the upper section. The transparent upper section permits a user to know a test is working by observing movement of urine and the reconstituted direct dye or labeled reagent along the flow path of the assay material from the fluid port region toward the capture region.

BRIEF DESCRIPTION OF THE DRAWINGS

The present invention will now be more particularly described with reference to the accompanying drawings, in which like items are identified by the same reference designation, which.

DETAILED DESCRIPTION OF THE INVENTION

In its most general application, the present invention provides an improved single-step device for detecting a pre-selected analyte in a urine stream. More specifically, use of the invention provides an easily readable, sensitive, reproducible indication of the presence of an analyte, such as human chorionic gonadotrophin (hCG) or luteinizing hormone (LH), in a urine stream. The invention also permits a user to immediately after applying a urine sample to assay material to determine a test is working.

As described herein above, the use of a single-step device, specifically a single-step device wherein the urine sample to be assayed is applied directly from a urine stream through a urine sample inlet port onto assay material enclosed within the casing of the device, may result in false or otherwise invalid test results. Recently, it has been discovered that the invalid test results may occur when the operator applies too much sample to the device which is turn results in flooding of the assay material enclosed within the device casing. It is believed that the flooding of the assay material prevents the sequential series of reactions that occur between the analyte and the analyte visualization reagents and/or the analyte capture reagents under optimal assay conditions. Accordingly, the single-step device and methods of the instant invention utilize an improved device casing that minimizes hydraulic pressure induced flooding of the assay material located within the casing thereby increasing the reliability of the test result. The casing also includes a transparent upper section for permitting a user to observe the movement of urine and the reconstituted direct labeled reagent in a flow path of the assay material to confirm a test is working.

In its broadest aspect, the improved device comprises an outer casing with a transparent upper section, and an assay material disposed therein. The assay material defines a capture region for binding an analyte of interest, i.e., hCG or LH. The outer casing defines the following elements which include: a hollow housing for receiving the assay material, a urine inlet port to permit urine applied directly from a urine stream to enter the casing and to contact the assay material; a window in a transparent upper section for viewing through the window the capture region on the assay material, and for viewing through the transparent upper section the movement of urine and the reconstituted direct labeled reagent in a flow path through the assay material to confirm a test is working. Optionally, at least one drainage vent may be provided to permit urine entering the casing via the urine inlet port to exit the casing thereby to inhibit hydraulic pressure induced flooding of the casing.

As used herein, the term "urine inlet port" is understood to mean any aperture defined by the outer casing that connects the hollow interior of the casing with the exterior of the casing. The urine inlet port, therefore, permits urine applied directly from a stream of urine to enter the casing and to contact assay material disposed therein. As used herein, the term "window" is understood to mean any aperture defined by the outer casing that connects the hollow interior of the casing with the exterior of the casing for viewing a capture region of the assay material, when the assay material is disposed within the casing. In a preferred embodiment the window for viewing the capture region of the assay material is spaced apart from the urine inlet port, and is provided in a transparent upper section of the casing. However, it is anticipated that in certain configurations the window and the urine inlet port may be defined by a single aperture. In the preferred embodiment, the urine inlet port and the viewing window are spaced apart such that urine inlet port and the viewing window are located on opposite sides of the casing. This configuration reduces the incidence of contamination of the capture region which is disposed in the interior of the casing. Also, the lower section of the casing is preferably opaque, but optionally can be provided by transparent material.

The casings useful in the practice of the instant invention also comprise means for minimizing hydraulically induced flooding of the test system when a urine stream is directed through the urine inlet port onto assay material disposed within the casing. The invention therefore may also include any means that prevents flooding of the assay material disposed therein.

In the preferred embodiment, the means for minimizing the hydraulically induced flooding of the casing comprises at least one drainage vent. As used herein, the term "drainage vent" is understood to mean any aperture defined by the outer casing that connects the hollow interior of the casing with the exterior of the casing and permits excess urine entering the casing through the urine inlet port to exit the casing. The drainage vent, therefore, dissipates the hydraulic pressure of the urine entering the casing and minimizes hydraulic pressure induced flooding of the assay material disposed therein. As used herein, the term "hydraulic pressure induced flooding" is understood to mean the accumulation of urine within the hollow casing when urine from a urine stream is directed into the casing in an amount sufficient to flood the assay material disposed therein.

The casing, therefore, may comprise one or more drainage vents which, either alone or in combination, permit urine entering the casing through the urine inlet port to exit the casing thereby to dissipate the hydraulic pressure of the urine entering the casing. Although it is anticipated that a variety of drainage vent configurations may be effective in dissipating the hydraulic pressure of urine entering the casing, the drainage vents preferably are spaced about the urine inlet ports. In addition, the drainage vents preferably are located upstream of a capture region disposed upon the assay material, and most preferably are located upstream of a release region also disposed upon the assay material. As described below, the release region on the assay material is located upstream of the capture region, therefore, if a drainage vent is upstream of the release region the drainage vent inherently is located upstream of the capture region. In a preferred embodiment of the invention, the casing defines a plurality of drainage vents, specifically three drainage vents, spaced about the urine inlet port to permit urine entering the casing via the fluid inlet port to exit the casing and to minimize hydraulic pressure induced flooding of the assay material disposed within the casing.

In another embodiment, the means for minimizing hydraulically induced flooding of the casing comprises a rib member that acts either on its own or in combination with a drainage vent. As used herein, the term "rib member" means any structural element in the casing, for example, a dam, that blocks or prevents hydraulically driven urine from flooding the assay material. Accordingly, the rib member provides another means for minimizing the amount of urine that traverses the assay material by a mechanism other than by sorptive transport.

The rib member may be defined either by one or more inner surfaces of the casing or may comprise a separate element that is inserted into the casing during assembly of the device. It is contemplated that whenever the rib is defined by an inner surface of the casing, the rib member is produced during the formation of the outer casing. In such a case, it is contemplated, therefore, that the rib is defined by the same moisture impervious material as is the outer casing. However, when the rib member is a separate element inserted into the casing during assembly of the device, it is anticipated that the rib may be produced from a moisture impermeable material other than the material used to produce the casing.

From the foregoing, it is appreciated that the outer casing of the device may take various forms. Typically, it will comprise an elongate casing comprising interfitting parts made of moisture impervious solid materials, for example, a plastic material. It is contemplated that a variety of commercially available plastics, including, but not limited to, polyvinyl chloride, polypropylene, polystyrene, polyethylene, polycarbonates, polysulfanes, polyesters, urethanes, and epoxies maybe used to produce casings useful in the practice of the instant invention. The device casings may be prepared by conventional methodologies, for example, standard molding technologies well known and used in the art. For example, the casings may be produced by molding technologies which include, but are not limited to, injection molding, compression molding, transfer molding, blow molding, extrusion molding, foam molding, and thermoform molding. The aforementioned molding technologies are well known in the art and so are not discussed in detail herein. See for example, *Processes And Materials Of Manufacture, Third Edition,* R. A. Lindsberg (1983) Allyn and Baron pp. 393–431.

Various embodiments of the present invention will now be described in greater detail with reference to the attached drawings, which are provided for purposes of illustration and not meant limit the scope of the present invention.

Figure 1A:
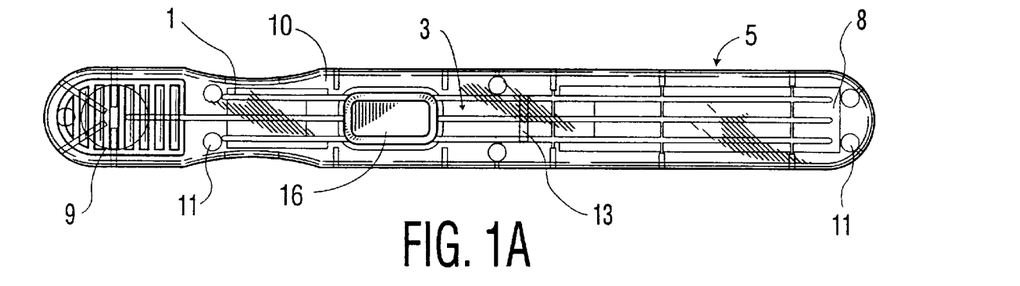
FIG. 1A is a top view of a first embodiment of a transparent upper section with a viewing window of a casing useful in the device of the present invention.
Figure 1B:
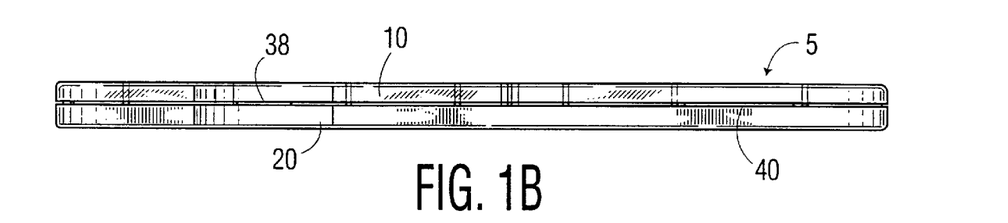
FIG. 1B is a longitudinal side view of the device of FIG. 1A showing the drainage vent.
Figure 1C:
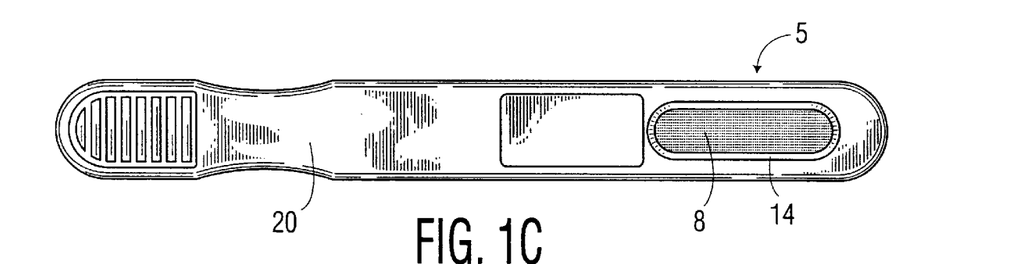
FIG. 1C is a bottom view of an opaque lower section of the casing of the device of FIG. 1A showing the urine inlet port.
Figure 1D:
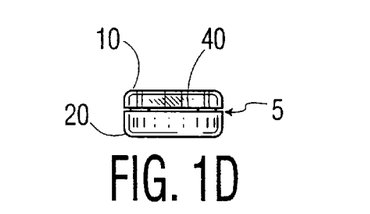
FIG. 1D is an end view of the proximal end of the device of FIG. 1A showing a drainage vent.
Figure 1E:
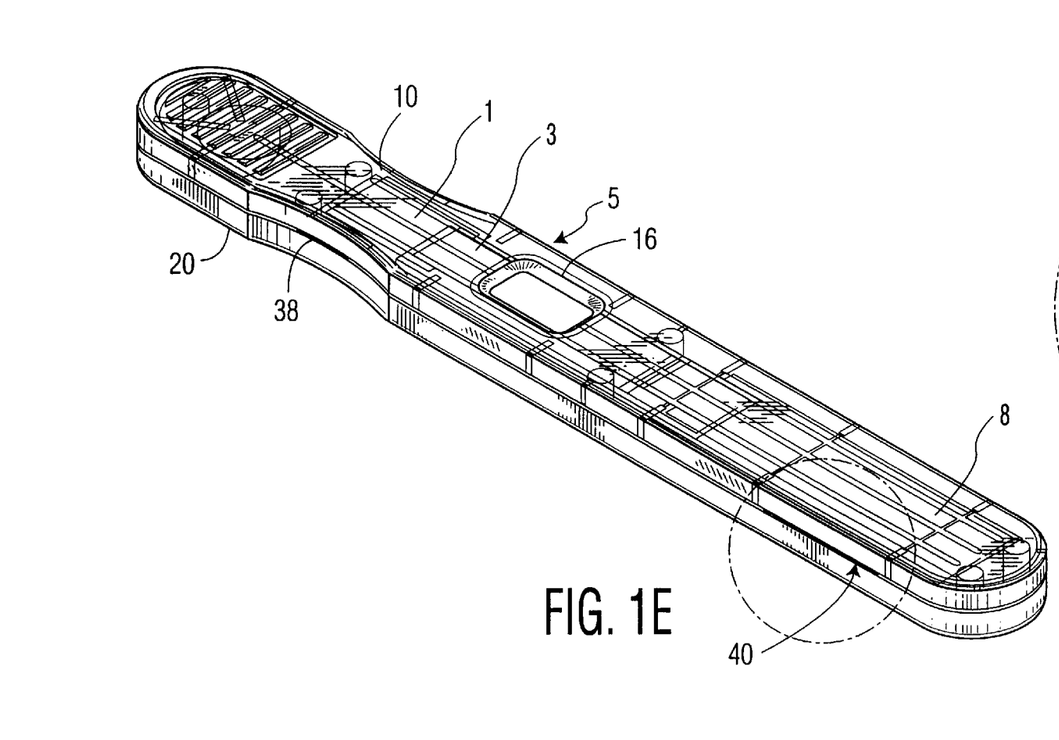
FIG. 1E is a perspective view of upper and side sections of a device constructed in accordance with one embodiment of the present invention.
Figure 1F:
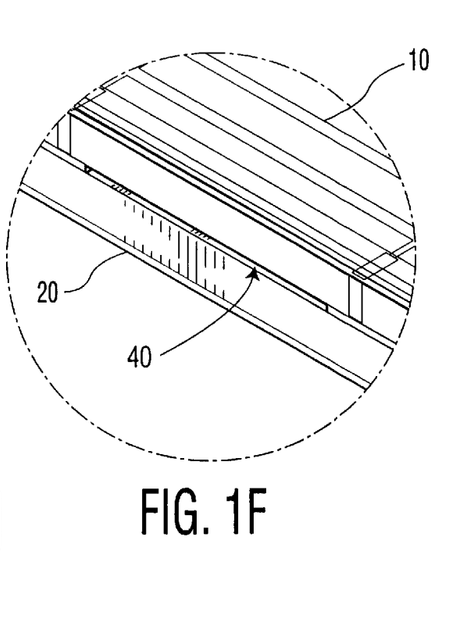
FIG. 1F is an exploded perspective view showing a drainage vent of the embodiment of FIG. 1E.
Figure 1G:
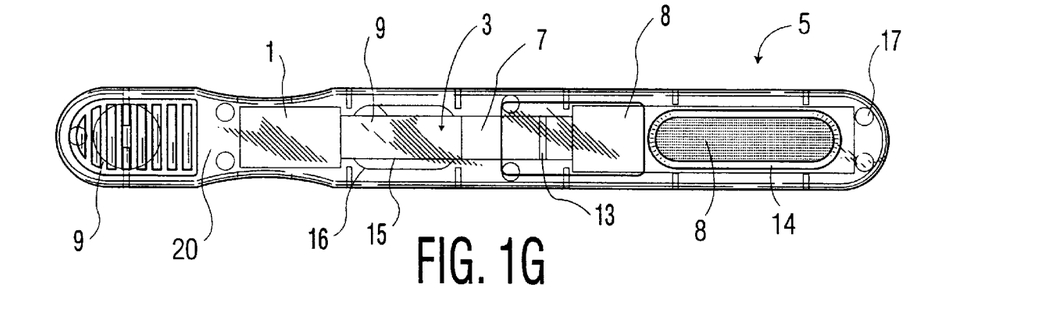
FIG. 1G is identical to FIG. 1C except that the lower section is transparent for another embodiment of the invention.
Figure 2A:
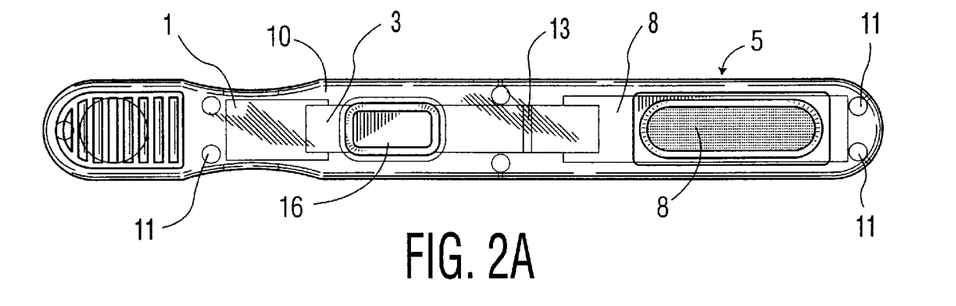
FIG. 2A is a top view of another embodiment of a casing useful in the device of the present invention showing a drainage vent and a viewing window.
Figure 2B:
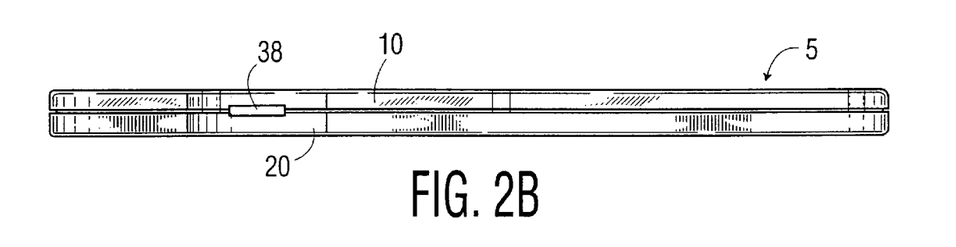
FIG. 2B is a longitudinal side view of the device of FIG. 2A.
Figure 2C:
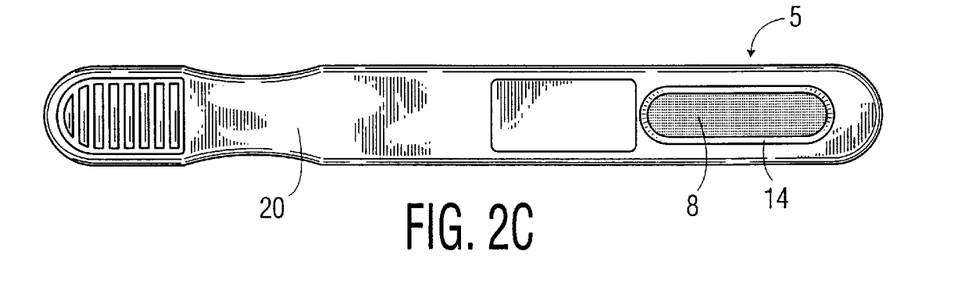
FIG. 2C is a bottom view of the device of FIG. 2A showing the urine inlet port.
Figure 2D:
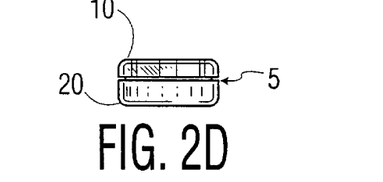
FIG. 2D is an end view of the proximal end of the device of 2A.
Figure 2E:
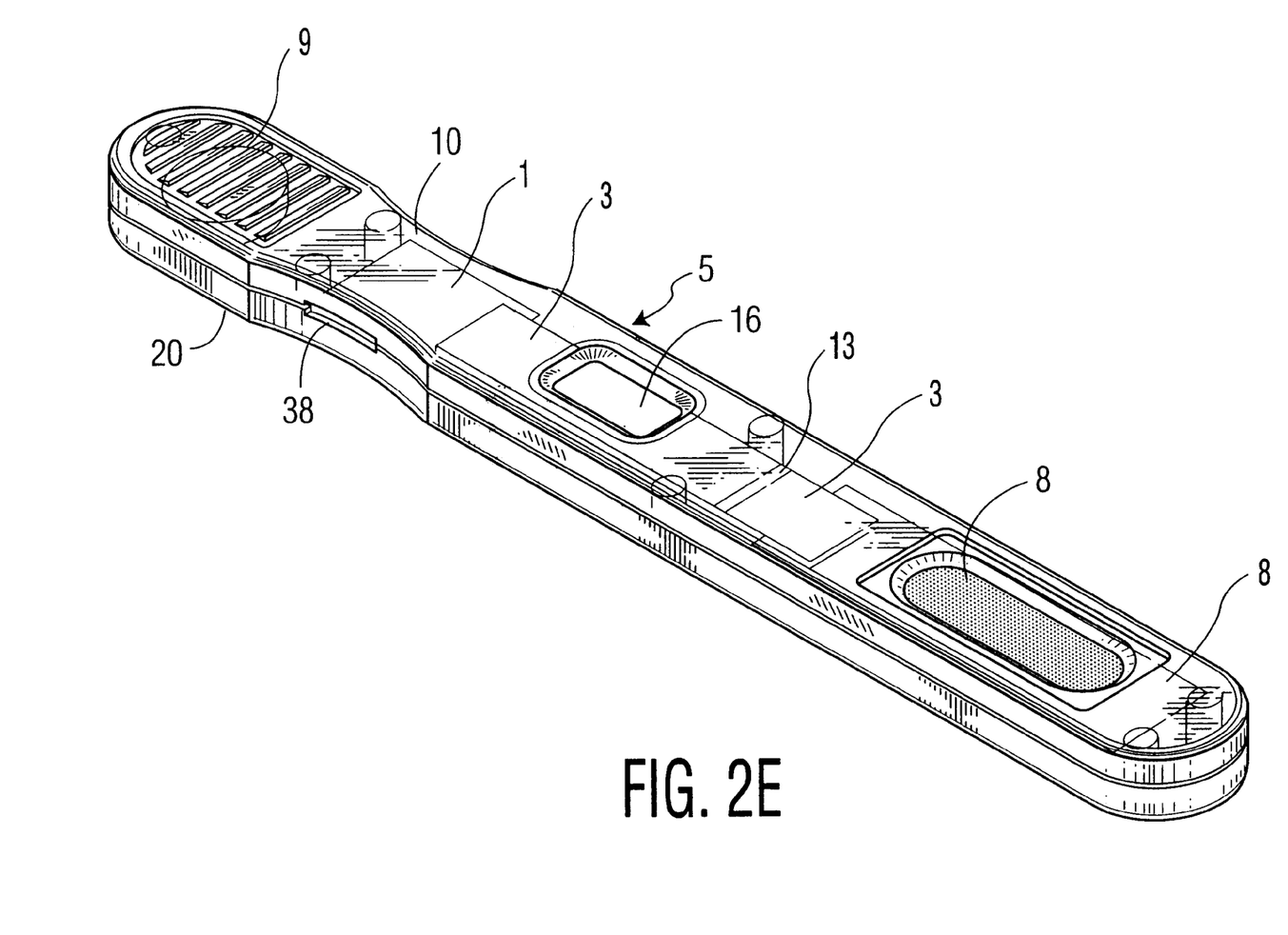
FIG. 2E is a perspective view of a device constructed in accordance with the present invention.
Figure 2F:
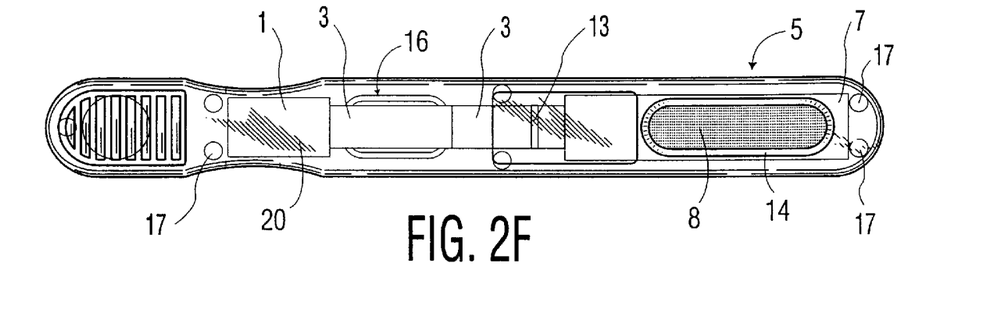
FIG. 2F is identical to FIG. 2C except that the lower section is transparent for another embodiment of the invention.
Figure 3A:
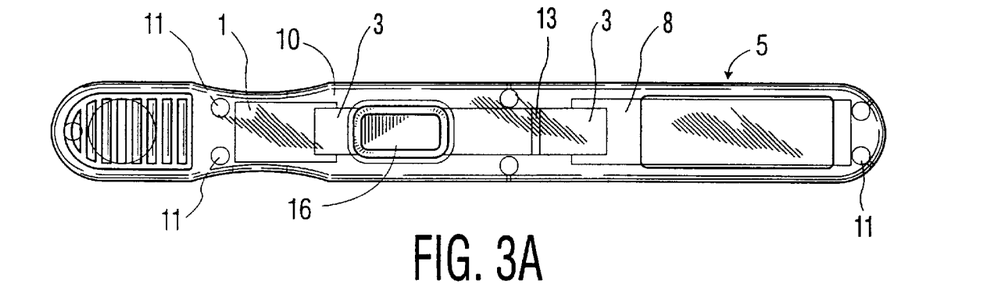
FIG. 3A is a top view of a third embodiment of a casing useful in the device of the present invention showing the window opening.
Figure 3B:
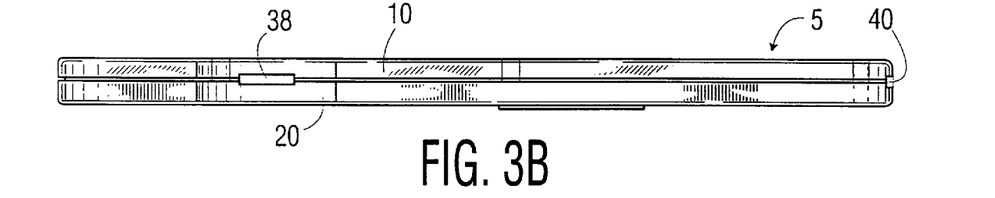
FIG. 3B is a longitudinal side view of the device of FIG. 3A.
Figure 3C:
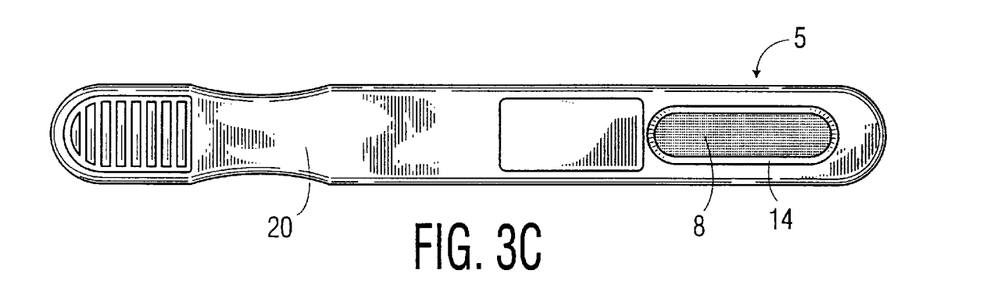
FIG. 3C is a bottom view of the device of FIG. 3A showing the urine inlet port.
Figure 3D:
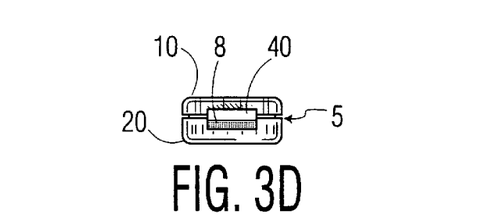
FIG. 3D is a end view of the proximal end of the device of FIG. 3A showing the drainage vent.
Figure 3E:
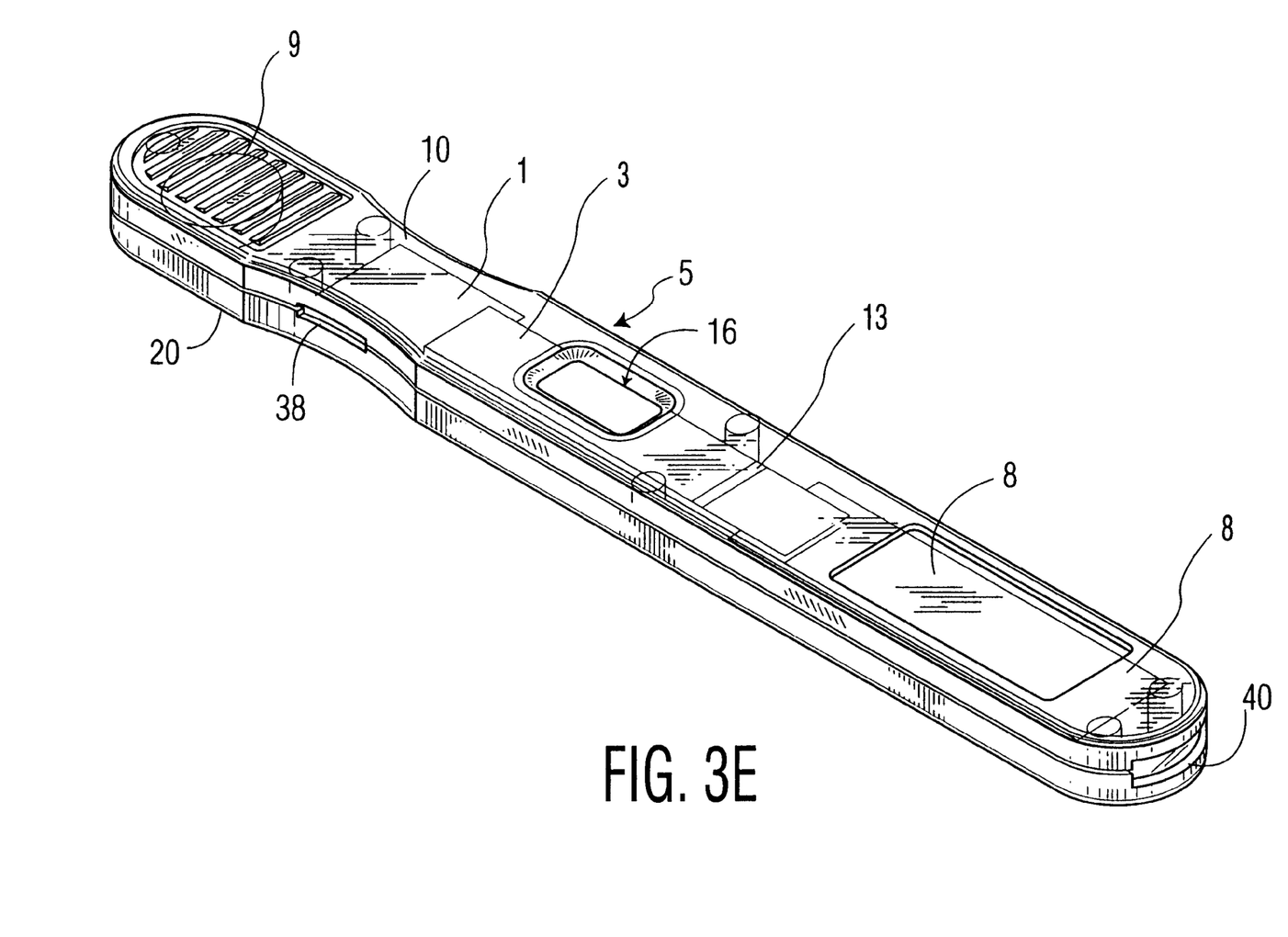
FIG. 3E is a perspective view of a device constructed in accordance with the present invention.
Figure 3F:
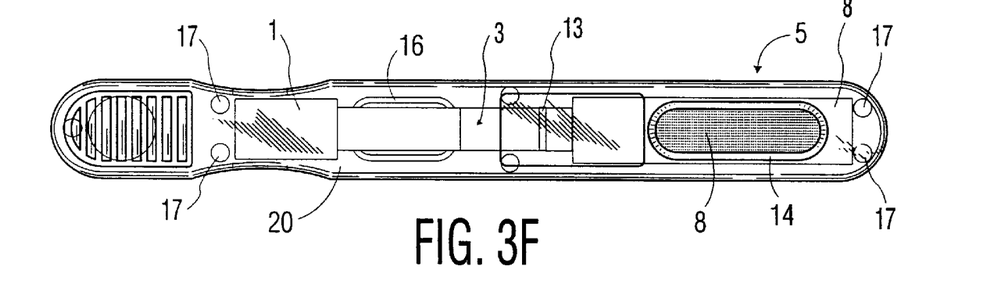
FIG. 3F is identical to FIG. 3C except that the lower section is transparent for another embodiment of the invention.

Referring to the drawings, FIGS. 1A through 1F illustrate schematically a first embodiment of a test device 5 constructed in accordance with the teachings of the present invention. The device comprises two interfitting sections 10 and 20, wherein 10 is a transparent upper section of the casing and 20 is a lower section of the casing. Conveniently, the two sections 10 and 20 may include means 11, 17 for interlocking the two sections 10 and 20 together. For example, the inner surface of one of the sections may contain protrusions which are designed to snap fit into protrusion receiving means located on the inner surface of the other section. The two sections 10 and 20, when interconnected, produce an outer casing that defines a hollow enclosure for receiving assay material 1, 3, 8. In a preferred embodiment the lower section 20 consists of opaque material, and optionally can consist of transparent material, as shown in FIG. 1G.

In addition, the outer casing defines a fluid inlet port 14 at a proximal end of the casing and a window 16 at a distal end of the casing through which the capture region on the assay material is visible. As illustrated in FIGS. 1A, 1C, and 1E window 16, defined by the upper section 10 of the casing, and fluid inlet port 14, defined by the lower section 20 of the casing, are disposed on opposite sides of the casing. This configuration reduces the incidence of contamination of the capture region which is disposed in the interior of the casing. The casing further defines two air displacement openings 38, each of which are located at a distal end of the casing on the sides of the casing where the upper section of the casing 10 mates with the lower section of the casing 20. The air displacement openings 38 permit air displaced by the addition of urine to the assay material 8 to exit the casing. The casing further defines three drainage vents 40, spaced about the fluid inlet port 14. In this embodiment, one drainage vent 40 is located at the extreme proximal end of the device 5 with the other two drainage vents 40 located in opposite sides of the device 5, specifically, where the upper section 10 of the casing mates with the lower section 20 of the casing. One of the latter drainage vents 40 is shown in the exploded perspective view, FIG. 1F. The drainage vents 40 are located to permit urine entering the casing through the urine inlet port 14 to exit the casing thereby inhibiting hydraulic pressure induced flooding of the casing. The presence of the drainage vents 40, therefore, reduces flooding of the assay material 1, 3, 8 disposed in the casing when the user applies too much sample to the device.

Referring to the drawings, FIGS. 2A through 2F and 3A through 3F illustrate schematically second and third embodiments of the invention, respectively. The first, second, and third embodiments differ only in the number and location of the drainage vents 40 defined by the casing. For example, in embodiment 2, FIGS. 2A through 2E show a single drainage vent 40 disposed apart from the window 16 in the transparent upper section 10 of the casing. In the second embodiment, the drainage vent 40 in the upper section 10 of the casing is positioned directly above the urine inlet port 14 in the lower section 20 of the casing. In the third embodiment, FIGS. 3A through 3F show a single drainage vent 40 located at the extreme proximal end of the device 5 where the upper section 10 of the casing mates with the lower section 20 of the casing. The lower section 20 is opaque in the embodiment of FIG. 2C, and transparent in the alternative embodiment of FIG. 2F.

It is contemplated that the casing may further define a control opening located downstream of, or distal to the window opening 16 for viewing a control region disposed on the assay material 1, 3, 8. Accordingly, the capture region preferably is disposed upon the assay material 3 downstream of the analyte capture region proximate window 16. The control regions enable the user to determine whether the device has functioned properly during usage. This same function is also provided in the preferred embodiment through use of a transparent upper section 10. Preferred control regions and the preferred reagents used therein are described in U.S. patent application Ser. 08/432,894, filed on May 2, 1995, the disclosure of which is incorporated herein by reference, as previously mentioned.

As used herein, the term "assay material" is understood to mean any material, preferably a sorptive material, that can be used to detect the presence of a pre-selected analyte in a urine sample. As used herein, the term "capture region" is understood to mean a region of the assay material capable of binding, either directly or indirectly, the pre-selected analyte. During direct binding, the pre-selected analyte binds to an immobilized binding partner, for example, an anti-analyte antibody immobilized within the capture region of the assay material 3. During indirect binding, the pre-selected analyte binds to a binding partner, for example, an anti-analyte antibody biotin conjugate, and the binding partner binds to a capture component, for example, streptavidin, immobilized within the capture region of the assay material.

As described herein, the assay material 1, 3, 8 may further define a urine sample application region provided by assay material 8. As used herein, the term "urine sample application region" is understood to mean a region, that preferably is disposed apart from the capture region provided by assay material 3, and positioned within the casing 10, 20 such when urine is applied directly from a urine stream to the urine inlet port, the urine enters the casing and contacts the urine sample application region. The urine application region 8 and the capture region 3 preferably are connected by a fluid flow path. The fluid flow path permits urine that contacts the urine sample application region 8 to flow to the capture region 3 by means of sorptive transport. Accordingly, it is understood that the capture region of the assay material 3 is located down stream of the urine sample application region 8. A user can observe the flow of urine and the reconstituted direct labeled reagent in the fluid flow path visible through the transparent upper section 10.

It is contemplated that the assay material may comprise a single element which where enclosed within the casing 10, 20 is capable of detecting the presence of analyte in a urine sample. Alternatively, the assay material may comprise several elements, such as elements 1, 3, and 8 as shown, which when enclosed with the casing 10, 20 cooperate with one another during the detection of the analyte in urine sample. For the purpose of understanding the present invention, however, the selection of the assay material is not critical, and indeed, it is contemplated that the invention may utilize a variety assay materials well known and described in the art.

In a particularly preferred embodiment, the assay material comprises three cooperating elements 1, 3, and 8, specifically a urine sample absorbent material 8, a biphasic chromatographic substrate 3, and a reservoir absorbent material 1, all of which are described in detail in copending U.S. application Ser. No. 08/432,894 filed on May 2, 1995. The urine sample absorbent material 8, the biphasic chromatographic substrate 3, and the reservoir absorbent material 1 are all in fluid communication with one another so that urine applied to the urine sample absorbent material 8 transverses the biphasic chromatographic substrate by sorptive transport until it reaches the reservoir absorbent material 1.

In the preferred embodiment, the urine sample absorbent material 8 is disposed within the casing adjacent to, and in fluid communication with the urine sample inlet port 14 and, therefore, acts as the urine sample application region. The absorbent material of the urine sample application region may further act as a filter to remove impurities, particulate matter, and interference factors from the urine sample. The urine sample absorbent material preferably is a bibulous hydrophilic material which facilitates absorption and transport of the urine sample to the biphasic chromatographic medium. Such materials may include cellulose acetate, hydrophilic polyester, or other materials having similar properties. A combination of absorbent materials also may be used. Preferred materials include bonded cellulose acetate, bonded polyolefin or hydrophilic polyester, such as those materials commercially available from American Filtrona Company (Richmond, Va.). Other preferred materials include absorbent papers such as Ahlstrom 939 or Ahlstrom 1281. The sample absorbent 8 preferably is coated with a buffered solution containing bovine serum albumin (BSA) and a nonionic surfactant, such as Trition X-100®. The presence of BSA and surfactant minimize non-specific absorption of the analyte. A concentration of about 3% BSA and about 0.1% surfactant are effective for this purpose.

In addition, the preferred embodiment comprises distal to, or downstream of, the urine sample absorbent material a biphasic chromatographic substrate defining a release region media 7 and a capture region media 9 joined together by the fluid flow path. In the preferred configuration, the release region media 7 is upstream of the capture region media 9. The release region media 7 preferably comprises absorbent paper, and the capture medium or region media 9 preferably comprises nitrocellulose membrane. The release region media 7 media and capture region media 9 preferably are both laminated onto a transparent plastic film or sheet 15. Disposed upon the release region media 7 is a first binding member comprising a first monoclonal antibody reactive with a first epitope on the analyte, and labeled with a visually detectable marker 13, such as, colloidal gold particles, and a capturable component comprising a biotinylated monoclonal antibody disposed downstream of the labeled antibody. In this example, the color of the marker 13 is purple. The biotinylated antibody is reactive with a second epitope on the analyte and is capable of forming a complex with the labeled antibody and the analyte. Also disposed upon the assay material 3 is a capture site for capturing and immobilizing the complex. The capture region having immobilized thereon a capture component, preferably streptavidin, which has a high affinity for the biotin portion of the complex.

The method for manufacturing the preferred biphasic chromatographic medium is described in copending U.S. application Ser. No. 08/434,342, filed on May 2, 1995, the disclosure of which is incorporated herein by reference as previously mentioned. Briefly, the release region media 7 and the capture region media 9 are positioned such that they overlap slightly, and an adhesive is disposed on the back of each (the back being the side opposite that which will receive reagents). The adhesive may be any pressure sensitive or hot melt adhesive which does not fill the pores of the release or capture region, thereby permitting unimpeded flow of the solvent front through the medium. Adhesive useful in the present invention are commercially available for example, from Adhesives Research Corporation. In a currently preferred embodiment, the adhesive is disposed on a clear polymer backing. The overlapping release and capture regions media 7, 9, respectively, then are packed through laminating rollers of a laminating machine together with the backed adhesive, forming a laminate of the capture and release media, the adhesive and the polymer backing. The resulting laminated biphasic substrate then is ready to receive the reagents, which are disposed as "stripes" onto the top of the substrate. Once the reagents have been deposited and dried, if necessary, the substrate is cut into desired size.

The diffusive and non-diffusive reagents can be applied to the release and capture reagents by any well known technique. In a currently preferred embodiment, the diffusable antibody reagents are applied to the release region by direct application onto the surface of the medium and dried to form a narrow band. The non-diffusable reagents are applied to the capture region by passive adsorption.

The preferred embodiment further comprises, reservoir absorbent material 1 disposed distal to, or downstream of, the biphasic chromatographic substrate 3 and in fluid communication therewith. By providing a reservoir of absorbent material 1 disposed beyond the biphasic chromatographic substrate, a relatively large volume of the urine and any analyte it contains may be drawn through the biphasic chromatographic substrate to aid sensitivity. The reservoir absorbent material 8 preferably comprises a hydrophilic material which may be the same as the urine sample application region absorbent. The purpose of the reservoir absorbent is to facilitate capillary action along the chromatographic substrate and to absorb excess urine contained with the casing 10, 20. The reservoir absorbent material 1 preferably comprises absorbent paper made from cotton long linter fibers, such as S&S 300, S&S 470, and S&S 900

(available from Schleicher & Schuell, Inc.) or cellulosic materials, such as Whatman 3MM (available from Whatman).

During operation of the preferred embodiment, urine from a urine stream is directed through the urine sample inlet port 14 and onto the sample application region of the assay material 8. The urine then passes by sorptive transport, for example, capillary action, wicking, or simple wetting, from the urine sample application region 8 to the biphasic chromatographic material 3 and finally to the reservoir material 1. During transportation through the biphasic chromatographic material 3 the urine first contacts the first monoclonal antibody located on the release region 7 (see FIGS. 1A and 1G). Upon contact with the urine, the first monoclonal antibody becomes reconstituted in the urine and then reacts with a first epitope on the pre-selected analyte, provided that the analyte is present within the urine sample. The first monoclonal antibody is labeled with a visually detectable marker such as colloidal gold. The urine while moving towards the capture region 9 contacts the second monoclonal antibody also located in the release region. Upon contact with the urine, the second monoclonal antibody also becomes reconstituted in the urine, and then reacts with the second epitope on the pre-selected analyte. The second monoclonal antibody is labeled with a capturable component such as biotin. The analyte, first monoclonal antibody, and the second monoclonal antibody, therefore, react to form a complex which subsequently can be captured when the complex reaches the capture region and contacts the streptavidin immobilized within the capture region 9.

In summary of the operation with reference to FIGS. 1A and 1G, a colloidal gold label antibody reagent 13 is deposited on release region 7 of assay material 3. When in this example, urine is applied to the sample absorbent material 8, the urine moves by capillary action or sorbent movement downstream toward window 16. When the urine contacts the reagent 13, it reconstitutes the reagent material, causing the reagent to move with the urine front along the flow path. The colored reagent movement is observable to a user at least through the transparent top casing section 10, thereby assuring the user that the test is effectively working. When the reconstituted marker reagent passes through the window region 16, capture means are included in the capture region 9 (see FIG. 1G) to cause a single colored line to appear indicative of no pregnancy, or a double line to appear indicative of pregnancy.

Broadly, the device and method of the invention may be used to detect any analyte which has heretofore been assayed using known immunoassay procedures, or is detectable by such procedure, using polyclonal antibodies or fragments thereof, monoclonal antibodies or fragments thereof, biosynthetic antibody binding sites or other proteins. Various specific assay protocols and reagents are known per se, see for example, U.S. Pat. No. 4,313,734, and U.S. Pat. No. 4,366,241.

It is, therefore, contemplated that the invention is not limited by the precise nature of the binding members. For example, polyclonal antibodies and fragments thereof or biosynthetic antibody sites, such as those disclosed in U.S. Pat. Nos. 5,091,513, and 5,132,405, and 5,258,498 may be substituted for the monoclonal antibodies disclosed herein. Accordingly polyclonal antibodies, monoclonal antibodies or biosynthetic antibody binding sites having specific binding properties and high affinity for virtually any antigenic substances which are useful in the present invention as binding and capture materials are publicly known and available. Alternatively, preferred monoclonal antibodies, polyclonal antibodies, or biosynthetic antibody binding sites may be prepared using techniques well known and thoroughly disclosed in the art. The literature is replete with protocols for producing and immobilizing antibodies. For example, the preparation of polygonal and monoclonal antibodies is disclosed in *Antibodies, A Laboratory Manual* (1988) Harlow and Lane, Cold Spring Harbor Press. The preparation of biosynthetic antibody binding sites is described in U.S. Pat. Nos. 5,091,513, and 5,132,405, and 5,258,498. Methods for immobilizing proteins are described in *Laboratory Techniques In Biochemistry And Molecular Biology,* Tijssen, Vol. 15, *Practice And Theory Of Enzyme immunoassay,* Chapter 13, Immobilization of Immunoreactants on Solid Phases, pp. 297 through 328 and all the references cited therein.

In another aspect, the invention provides a method for producing an improved device for detecting the presence of an analyte in a urine stream. The method comprises providing an assay material having at least an analyte capture region for binding the analyte. The method also comprises the step of providing an outer casing. The casing defines: a hollow housing 10, 20 for receiving the assay material; a urine inlet port 14 to permit urine applied directly from a urine stream to enter the casing 10, 20 and to contact the assay material 8; a window 16 spaced apart from the urine inlet port 14 for viewing the capture region; and at least one drainage vent 40 to permit excess urine entering the casing 10, 20 through the urine inlet port 14 to exit the casing 10, 20 and thereby to minimize hydraulic flooding of the casing 10, 20. Finally, the method comprises the step of enclosing the assay material 1, 3, 8 within the casing 10, 20, and making at least the upper section transparent 10 for permitting a user to observe the movement of urine and the reconstituted direct labeled reagent through a flow path in the assay material 3 and 8 from the urine inlet port 14 region to the window 16 region.

The present invention will now be further particularly described with reference to the following exemplification. In the exemplification, the test devices are described with reference to FIGS. 1A through 1G, and FIGS. 2A through 2F of the accompanying drawings which have been described herein above.

Exemplification, Pregnancy Test

In this exemplification, the performance of three types of pregnancy test devices was evaluated. The only difference between the three devices was the number and configuration of drainage vents in the casing of each device. The assay materials disposed within each casing were identical.

In a first device 5, as depicted in FIGS. 1A through 1G, the casing includes three drainage vents 40 spaced about the urine inlet port 14. Briefly, one drainage vent was located at the extreme proximal end of the casing with the two remaining drainage vents located along each side of the casing. Furthermore, in this device 5 the urine inlet port 14 and the viewing window 16 were disposed on opposite sides of the casing 10, 20. In a second device 5, as depicted in FIG. 2A through 2F, the casing 10, 20 includes a single drainage vent 40 located on the same side of the casing 10 as the viewing window 16 but on an opposite side of the casing 20 from the urine inlet port 14. In a third device, the casing 10, 20 of the device 5 did not contain a drainage vent.

The casing 10, 20 for each device 5 has a rectangular shape, and is formed from polystyrene by injection molding, in this example. For each device 5, two interlocking sections, specifically an upper section 10 and a lower section 20, were prepared wherein the inner surface of the lower section 20 of the casing includes protrusions 11 designed to snap fit into protrusion receiving means 17 defined by the inner surface of the upper section 10 of the casing. The assay material includes a urine sample absorbent material 8, a biphasic chromatographic substrate 3, and a reservoir absorbent material 1, that is enclosed within the casing 10, 20 to produce the device 5.

The same assay material array 1, 3, 8 was used in each of the three devices 5. Briefly, in this example, the urine sample absorbent material 8 acting as the urine sample application region is bonded hydrophilic polyester; the release medium 7 on the biphasic chromatographic substrate 3 is S&S 903 paper (Schleicher & Schuell); the capture medium 9 on the biphasic chromatographic substrate 3 is nitrocellulose membrane. The release and capture media 7, 9, respectively, of the biphasic chromatographic substrate 3 are laminated onto polyethylene, terephthalate 15 precoated with an adhesive. The reservoir absorbent material 1 was S&S 300 paper (Schleicher & Schuell). The dimensions of the urine sample absorbent material 8 were approximately 5.0×1.27×0.25 cm (2.0×0.5×0.1 inches) on each side. The dimensions of release medium 7 of the biphasic chromatographic substrate 3 were approximately 2.8×0.8×0.06 (1.1×0.32×0.025 inches) and for the capture medium 9, approximately 2.5× 0.8×0.018 cm (1×0.32×0.007 inches). The dimensions of the reservoir absorbent pad 1 were approximately 2.0×0.26× 1.06 cm (0.8×0.1×0.4 inches). A number of these substrates were produced and further treated to adapt them for the detection of hCG in urine. The test reagents were anti-hCG monoclonal antibody 2G9 (Carter-Wallace) conjugated with 15–30nm colloidal gold particles (Carter-Wallace); biotinylated anti-hCG specific monoclonal antibody CCF01 (Carter-Wallace), and streptavidin. The quantities of reagents used in each single-step device were 0.048 $OD_{533nm}$ 2G9 gold conjugate; 0.1 µg biotin conjugated CCF01; and 0.8 µg streptavidin. The reagents were disposed upon the assay material 1, 3, 8 in the format as described above.

Protocol I—Case Study

Fifty (50) women were each given one (1) of the three (3) single-step devices 100, 200, and 300, respectively, and asked to urinate for at least 10 seconds through the urine sample inlet port 14 onto the urine sample region of the assay material 8. Each woman was to note the urination time and to record the time at which they could read a result. A monitor (a Carter-Wallace representative) also read the test result and recorded the result time. The consumers used drawings of positive, negative, and invalid results to guide them; they received no help from the monitor. The consumers were asked to watt five (5) minutes before calling a result invalid. The devices 100, 200, 300 were weighed before and after testing to determine the sample volume absorbed. The performance of each device 100, 200, 300 is summarized in Table I below.

It was found that all the devices 100, 200, 300 used approximately the same amount of urine to perform the assay and that all of the devices 100, 200, 300 had approximately the same completion time. It was found, however, that the introduction of drainage vents such as 40 into the casing of devices 100 and 200 resulted in significantly higher accuracy and fewer invalid test results caused by the flooding of the assay material 1, 3, 8 enclosed within the device casing 10, 20. For example, 5% of the results using device 300, which had no drainage vents, were invalid because the assay material flooded. In contrast, none of the results using either devices 100 or 200, having the drainage vents, were invalid because of flooded assay material. Therefore, the introduction and placement of drainage vents 40 in the casing 10, 20 dramatically improved the accuracy and reliability of the assay results.

TABLE I

| Device Type | Device 100 | Device 200 | Device 300 |
| --- | --- | --- | --- |
| Average urination time. | 15.4 seconds | 15.0 seconds | 16.0 seconds |
| Average completion time | 1.48 minutes | 1.34 minutes | 1.52 minutes |
| % Devices run within 2 minutes | 75% | 86% | 71% |
| % Devices run within 2 and 3 minutes | 21% | 12% | 20% |
| % Devices run within 3 and 5 minutes | 0% | 2% | 2% |
| % Devices run longer than 5 minutes | 2% | 0% | 2% |
| Average Sample uptake. | 1.62 ml | 1.57 ml | 1.69 ml |
| % Invalid Results Due to Sample Flooding | 0% | 0% | 5% |

Protocol II—High Flow Test Study

In another set of experiments designed to simulate midstream use, replicate tests were performed by adjusting the flow of water from a tap to rate of 60–70 ml/sec and directing the water stream to the sample inlet port at the proximal end of each of the three devices 100, 200, 300. The tests were developed and the results summarized in Table II.

The results show that during the use of devices 100 and 200 no invalid test results caused by flooding of the assay material occurred. On the other hand, with device 300 having no drainage vents, 20% of the results were invalid due to hydraulic pressure flooding of the assay material. The drainage vents, therefore, dramatically improved the reliability of the assay results by minimizing the incidence of hydraulic pressure induced flooding of the assay material located within the casing of device 100 and 200.

TABLE II

| Device Type | Device 100 | Device 200 | Device 300 |
| --- | --- | --- | --- |
| % invalid with high flow tap test | 0% | 0% | 20% |

Other Embodiments

Those of skill in the art may recognize certain modifications to the various embodiments of the invention, which modifications are meant to be covered by the spirit and scope of the appended claims.

What is claimed is:

1. A device for detecting the presence of an analyte in a urine stream, the device comprising:

an assay material including in one portion a capture region for binding the analyte, and in another portion a urine sample receiving region; and a casing defining:

a hollow housing enclosing the assay material, said housing having an upper section co-joined to a lower section;

a urine inlet port located proximate one end of the lower section to permit urine applied directly from a urine stream to enter the casing and to contact the urine sample receiving region of said assay material;

a window in said upper section spaced apart from the vertical plane of the urine inlet port, said window providing viewing of the capture region; and at least said upper section being transparent for permitting a user, immediately after applying urine into said urine inlet port, to observe movement of urine and a reconstituted direct labeled reagent along a flow path of said assay material from proximate said urine sample region toward said capture region, to thereby determine that a test is working.

2. The device of claim 1, further including at least one drainage vent to permit excess urine entering the casing through the urine inlet port to exit the casing thereby to minimize hydraulic flooding of the casing.

3. The device of claim 1, wherein the assay material comprises a sorptive material defining said urine sample receiving region spaced apart from the capture region which permits sorptive transport of urine.

4. The device of claim 1, wherein said lower section consists of transparent material.

5. The device of claim 1, wherein said casing is rectangular.

6. A device for detecting the presence of an analyte in a urine stream, the device comprising:

an assay material comprising a sorptive material defining a urine sample application region spaced apart from a capture region which permits sorptive transport of urine; and a casing defining:
 a hollow housing for receiving the assay material, said housing having an upper section of transparent material co-joined to a lower section;
 a urine inlet port to permit urine applied directly from a urine stream to enter the casing and to contact the assay material;
 a window spaced apart from the urine inlet port for viewing the capture region; and
 at least one drainage vent to permit excess urine entering the casing through the fluid inlet port to exit the casing thereby minimizing hydraulic flooding of the casing;

the assay material being disposed within the casing such that when a urine stream is directed through the urine inlet port onto the urine sample application region, the analyte moves by sorptive transport along the assay material and binds to binding material in the capture region, wherein such movement of analyte can be viewed through the transparent upper section to confirm an operative test is in process.

7. The device of claim 6, wherein the casing further includes three drainage openings spaced about the urine inlet port.

8. The device of claim 6, wherein the window is located on a side of the casing opposite from the urine inlet port.

9. The device of claim 6, further comprising a rib member defining a dam positioned within the casing to inhibit hydraulically driven urine from flooding the casing.

10. The device of claim 9, wherein an inner surface of the casing defines the rib.

11. The device of claim 6, wherein said casing is rectangular.

12. A device for detecting the presence of an analyte in a urine stream, the device comprising:

an assay material comprising a sorptive material defining a urine sample application region spaced apart from a capture region which permits sorptive transport of urine; and a casing defining:
 a hollow housing for receiving the assay material, said housing having an upper section of transparent material co-joined to a lower section;
 a urine inlet port to permit urine applied directly from a urine stream to enter the casing and to contact the assay material;
 a window spaced apart from the urine inlet port for viewing the capture region; and
 said window being located on a side of the casing opposite from the urine inlet port;

the assay material being disposed within the casing such that when a urine stream is directed through the urine inlet port onto the urine sample application region, the analyte moves by sorptive transport along the assay material and binds to binding material in the capture region, wherein such movement of analyte can be viewed through the transparent upper section to confirm an operative test is in process.

13. The device of claim 12, further including at least one drainage vent to permit excess urine entering the casing through the fluid inlet port to exit the casing thereby minimizing hydraulic flooding of the casing.

14. The device of claim 12, wherein the casing further includes three drainage openings spaced about the urine inlet port.

15. The device of claim 12, further comprising a rib member defining a dam positioned within the casing to inhibit hydraulically driven urine from flooding the casing.

16. The device of claim 15, wherein an inner surface of the casing defines the rib.

17. The device of claim 12, wherein said casing is rectangular.

18. A device for detecting the presence of an analyte in a urine stream, the device comprising:

an assay material comprising a sorptive material defining a urine sample application region spaced apart from a capture region which permits sorptive transport of urine;

a casing defining:
 a hollow housing for receiving the assay material, said housing having an upper section of transparent material co-joined to a lower section;
 a urine inlet port to permit urine applied directly from a urine stream to enter the casing and to contact the assay material;
 a window spaced apart from the urine inlet port for viewing the capture region; and
 a rib member defining a dam positioned within the casing to inhibit hydraulically driven urine from flooding the casing;

the assay material being disposed within the casing such that when a urine stream is directed through the urine inlet port onto the urine sample application region, the analyte moves by sorptive transport along the assay material and binds to binding material in the capture region, wherein such movement of analyte can be viewed through the transparent upper section to confirm an operative test is in process.

19. The device of claim 18, further including at least one drainage vent to permit excess urine entering the casing through the fluid inlet port to exit the casing thereby minimizing hydraulic flooding of the casing.

20. The device of claim 18, wherein the casing further includes three drainage openings spaced about the urine inlet port.

21. The device of claim 18, wherein the window is located on a side of the casing opposite from the urine inlet port.

22. The device of claim 18, wherein an inner surface of the casing defines the rib.

23. The device of claim 18, wherein said casing is rectangular.

* * * * *